United States Patent
Lozinsky et al.

(10) Patent No.: US 9,789,106 B2
(45) Date of Patent: *Oct. 17, 2017

(54) FOAMABLE OTIC PHARMACEUTICAL COMPOSITIONS

(71) Applicant: OTIC PHARMA LTD., Rehovot (IL)

(72) Inventors: Evgenia Lozinsky, Beer-Sheva (IL); Yanna Galibov, Kiryat Gat (IL); Rodrigo Yelin, Kfar Yona (IL)

(73) Assignee: OTIC PHARMA LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/385,460

(22) Filed: Dec. 20, 2016

(65) Prior Publication Data

US 2017/0105991 A1    Apr. 20, 2017

Related U.S. Application Data

(63) Continuation of application No. 14/655,753, filed as application No. PCT/IL2013/051069 on Dec. 26, 2013, now Pat. No. 9,561,240.

(60) Provisional application No. 61/745,820, filed on Dec. 26, 2012.

(51) Int. Cl.

| A61K 31/496 | (2006.01) |
|---|---|
| A61K 9/107 | (2006.01) |
| A61K 45/06 | (2006.01) |
| A61K 47/06 | (2006.01) |
| A61K 47/10 | (2017.01) |
| A61K 47/26 | (2006.01) |
| A61K 47/12 | (2006.01) |
| A61K 47/20 | (2006.01) |
| A61K 47/38 | (2006.01) |
| A61K 47/32 | (2006.01) |
| A61K 9/12 | (2006.01) |
| A61K 9/00 | (2006.01) |

(52) U.S. Cl.
CPC .......... *A61K 31/496* (2013.01); *A61K 9/0046* (2013.01); *A61K 9/107* (2013.01); *A61K 9/122* (2013.01); *A61K 45/06* (2013.01); *A61K 47/06* (2013.01); *A61K 47/10* (2013.01); *A61K 47/12* (2013.01); *A61K 47/20* (2013.01); *A61K 47/26* (2013.01); *A61K 47/32* (2013.01); *A61K 47/38* (2013.01)

(58) Field of Classification Search
CPC ...... A61K 31/496; A61K 9/107; A61K 45/06; A61K 47/06; A61K 47/10; A61K 9/122; A61K 9/0046; A61K 47/26; A61K 47/12; A61K 47/20; A61K 47/38; A61K 47/32

See application file for complete search history.

(56) References Cited

U.S. PATENT DOCUMENTS

| 4,744,979 | A | 5/1988 | Osipow |
|---|---|---|---|
| 5,188,832 | A | 2/1993 | Mehlhorn |
| 5,843,930 | A | 12/1998 | Purwar |
| 6,359,016 | B2 | 3/2002 | Singh |
| 6,462,033 | B2 | 10/2002 | Singh |
| 6,730,288 | B1 | 5/2004 | Abram |
| 7,078,058 | B2 | 7/2006 | Jones |
| 7,186,416 | B2 | 3/2007 | Popp |
| 7,700,076 | B2 | 4/2010 | Tamarkin |
| 8,030,362 | B2 | 10/2011 | Eilat |
| 8,636,982 | B2 | 1/2014 | Tamarkin |
| 2004/0186098 | A1 | 9/2004 | Magal |
| 2006/0226249 | A1 | 10/2006 | Ketcha |
| 2006/0233721 | A1 | 10/2006 | Tamarkin |
| 2008/0075670 | A1* | 3/2008 | Eilat ................. A61K 9/0046 424/43 |
| 2008/0124385 | A1 | 5/2008 | Campbell |
| 2008/0167281 | A1* | 7/2008 | Preston ................. A61K 31/24 514/171 |
| 2011/0236321 | A1 | 9/2011 | Trumbore |
| 2012/0252720 | A1 | 10/2012 | Eilat |

FOREIGN PATENT DOCUMENTS

| WO | 03026671 | 4/2003 |
|---|---|---|
| WO | 2006129161 | 12/2006 |
| WO | 2010143186 | 12/2010 |

OTHER PUBLICATIONS

Marom et al., (2010) Comparison of safety and efficacy of foam-based versus solution-based ciprofloxacin for acute otitis extema. Otolaryngol Head Neck Surg 143(4): 492-9.
Science Lab.com's Material Safety Data Sheet for Cetyl Alcohol; 5 pages, last updated on May 21, 2013, created on Oct. 9, 2005.
Supplemental European Search Report from a counterpart foreign application (EP 13 86 7062) mailed on Jun. 10, 2016 (9 pages).

* cited by examiner

*Primary Examiner* — Blessing M Fubara
(74) *Attorney, Agent, or Firm* — Roach Brown McCarthy & Gruber, P.C.; Kevin D. McCarthy

(57) ABSTRACT

The present invention relates a foamable otic pharmaceutical compositions comprising oil-in water emulsions which comprise an antibiotic agent and a propellant gas. The pharmaceutical compositions are administered to the ear as foam for treating ear disorders.

17 Claims, 1 Drawing Sheet

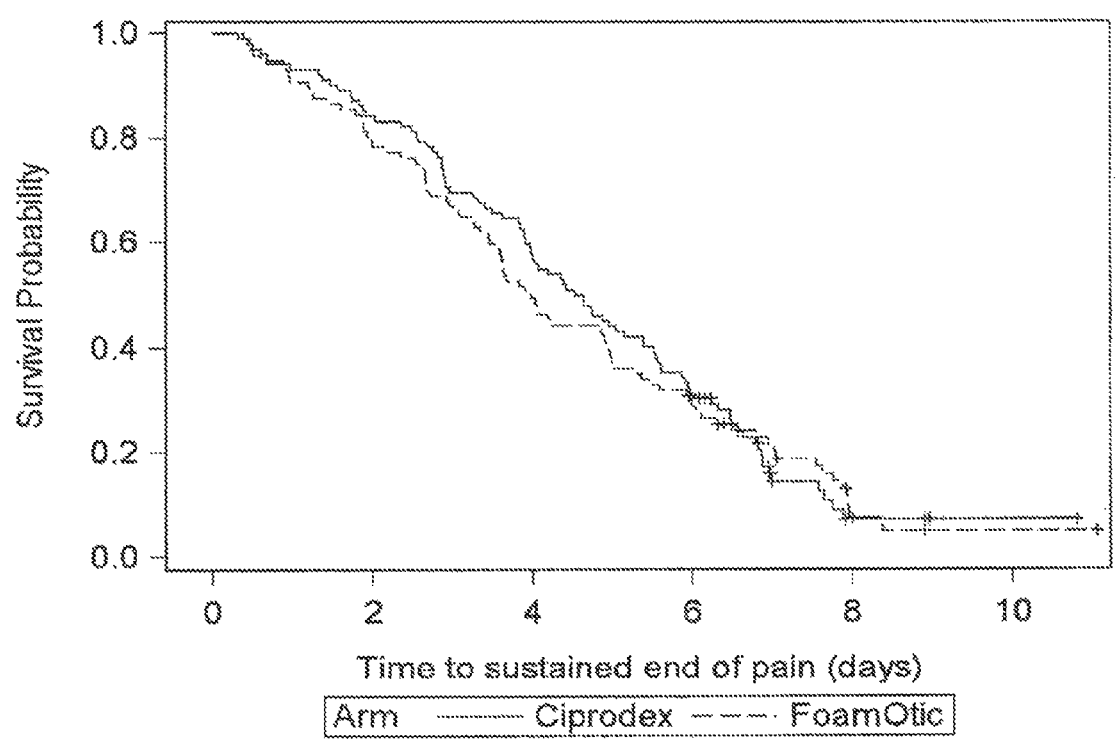

FOAMABLE OTIC PHARMACEUTICAL COMPOSITIONS

FIELD OF THE INVENTION

The present invention relates to foamable otic pharmaceutical compositions comprising oil-in-water emulsions which comprise an antibiotic agent and a propellant gas. The pharmaceutical compositions are administered to the ear in the form of foam for treating ear disorders.

BACKGROUND OF THE INVENTION

Otitis externa which involves the ear canal portion of the external ear is a common otologic problem occurring in humans mainly during hot and humid weather. Otitis externa is five times more frequent in swimmers than in non-swimmers. It is an acute or chronic inflammation of the epithelium of the external ear canal. It may develop anywhere from the tympanic membrane to the pinna. It is variably characterized by erythema, edema, increased sebum or exudates, and desquamation of the epithelium. In later stages, suppuration occurs in the ear canal and hearing may be decreased. Over 90% of cases of acute Otitis Externa (AOE) are due to bacterial infections.

Otitis externa is the most common disease of the ear canal in dogs and cats, and is occasionally seen in rabbits (in which it is usually due to the mite Psoroptescuniculi).

Otitis media involves infections of the middle ear and it is a very common otologic problem in adults and particularly in children. It has been estimated that nearly 95% of all children experience one or more episodes of otitis by age 9, and that about 15% of all visits by children to pediatricians are due to otitis media. In children, the disease is often associated with upper respiratory afflictions which trigger a transudate secretion response in the Eustachian tube and middle ear. Bacteria and viruses migrate from the nasopharynx to the middle ear via the Eustachian tube, and can cause the Eustachian tube to become blocked, preventing ventilation and drainage of the middle ear.

The common treatment of AOE consists of topical antibiotics, with or without steroids, analgesia and water avoidance. Otic preparations are generally supplied in the form of ear drops. Antibiotic agents in ear drops include aminoglycosides (mainly neomycin) in combination with polymyxin B and hydrocortisone or fluoroquinolones such as ciprofloxacin and ofloxacin.

Ciprofloxacin is a safe and efficacious antibacterial fluoroquinolone active against a broad spectrum of gram-positive and gram-negative bacteria. Ciprofloxacin is present as Ciprofloxacin base and Ciprofloxacin HCl.

Due to its proven safety and lack of ototoxicity, sterile ciprofloxacin ear drops are prescribed to treat patients with AOE with intact or non-intact tympanic membrane. Topical otic compositions containing a combination of either ciprofloxacin and hydrocortisone or ciprofloxacin and dexamethasone are sold under the name of CIPRO HC™ and CIPRODEX™, respectively, by Alcon Laboratories, Inc.

U.S. Pat. No. 5,843,930 to Purwar et al. discloses a liquid non-ototoxic, topical, otic pharmaceutical composition for the treatment of otitis externa and otitis media which comprises ciprofloxacin, a non-ionic viscosity augmenter, a preservative, water sufficient to produce an aqueous composition, hydrocortisone in aqueous suspension, lecithin, and polysorbate 20 to 80. U.S. Pat. No. 5,843,930 further discloses methods for treating otitis which comprise administering the otic pharmaceutical composition topically into the ear.

U.S. Pat. No. 6,359,016 to Singh et al., discloses aqueous suspension formulations comprising ciprofloxacin, dexamethasone, sodium chloride as an ionic tonicity agent, a nonionic polymer, and a nonionic surfactant. The formulations according to U.S. Pat. No. 6,359,016 have a pH from 3-5 that can be adjusted by NaOH/HCl and comprise the buffering system of sodium acetate and acetic acid. According to U.S. Pat. No. 6,359,016, the formulations may further comprise quaternary ammonium halide as a preservative and a chelating agent.

U.S. Pat. No. 6,462,033 to Singh discloses method for preparing a topical composition comprising ciprofloxacin and hydrocortisone. The compositions of U.S. Pat. No. 6,462,033 have excellent physical stability attributed to the method of their preparation, i.e., hydrocortisone is dispersed with lecithin and optionally with a polysorbate surfactant for greater than 45 minutes prior to combining hydrocortisone with the remainder of the composition.

U.S. Pat. No. 6,730,288 to Abram discloses pharmaceutical aerosol foam compositions which include a pharmaceutically active ingredient, an occlusive agent, an aqueous solvent, and an organic cosolvent, wherein the pharmaceutically active ingredient being insoluble in both water and the occlusive agent. The pharmaceutical compositions according to U.S. Pat. No. 6,730,288 are useful for topical administration of the pharmaceutically active ingredients on the skin.

U.S. Pat. No. 7,078,058 to Jones et al. discloses foamable pharmaceutical compositions comprising a corticosteroid, a quick-break foaming agent, a propellant and a buffering agent. According to U.S. Pat. No. 7,078,058, the quick-break foaming agent comprises an aliphatic alcohol, water, a fatty alcohol and a surface active agent. The compositions of U.S. Pat. No. 7,078,058 are especially well-suited for use in the treatment of various skin diseases, and in particularly in the treatment of scalp psoriasis.

U.S. Pat. No. 7,186,416 to Popp et al. discloses foamable delivery systems which comprise a solvent composition, a surfactant composition, a propellant and an acid, particularly useful for dermatological administration of corticosteroids and antifungal agents.

U.S. Pat. No. 7,700,076 to Tamarkin et al. discloses an alcohol-free cosmetic or pharmaceutical foam composition comprising water, a hydrophobic solvent, a surface-active agent, a gelling agent, an active component selected from the group of urea, hydroxyl acid, and a therapeutic enhancer and a propellant. The foam according to U.S. Pat. No. 7,700,076 further comprises active agents and excipients with therapeutic properties having enhanced skin penetration.

U.S. Pat. No. 8,030,362 to Eilat discloses a pharmaceutical composition for the treatment of an ear disorder in a form selected from foam and mousse comprising: a pharmaceutical agent known to affect an ear disorder; a pharmaceutically acceptable carrier comprising a dispersing agent that is a foam forming agent; and a dispensing device adapted for the dispensing of the pharmaceutical agent admixed with the carrier to the external auditory meatus.

International Patent Application Publication No. WO 2010/143186 assigned to the applicant of the present invention discloses a foamable otic pharmaceutical composition comprising an oil-in-water emulsion which comprises a fluoroquinolone, a hydrophobic solvent, an emulsifier and/or a synthetic surfactant, a stabilizing agent, a polar co-solvent, and water; and a compressed propellant gas, wherein the composition packaged in a container is adapted to form foam after dispensing from the container, the foam having a density of about 0.1 gr/ml to about 0.5 gr/ml.

U.S. Patent Application Publication No. 2006/0233721 discloses a foamable oil-in-water emulsion composition which includes: (a) an oil globule system selected from the group consisting of oil bodies and sub-micron oil globules; (b) about 0.1% to about 5% by weight of at least one stabilizing agent selected from the group consisting of a non-ionic surfactant having an HLB value between 9 and 16, an ionic surfactant, and a polymeric agent; and (c) a liquefied or compressed gas propellant.

There is an unmet need for formulations comprising clinically efficacious compositions of an antibiotic agent which upon dispensing from a container form a stable dosage form retained in the patient's ear so as to treat ear disorders.

SUMMARY OF THE INVENTION

The present invention provides foamable pharmaceutical compositions useful for otic administration which comprise an oil-in-water emulsion comprising an antibiotic agent, optionally further comprising a steroid anti-inflammatory agent, and a propellant gas. Particularly, the present invention provides otic foamable pharmaceutical compositions comprising an oil-in-water emulsion comprising a quinolone antibiotic agent such as ciprofloxacin and a propellant gas, and use thereof for treating otitis. The present invention has improved properties in comparison to previously known compositions intended for the same use, in particular in regard to the residence time and tackiness such that the foam formulation performs better and has increased efficacy in clinical trials.

It is now disclosed that foamable compositions of the invention comprising an oil-in-water emulsion and a compressed propellant gas, when dispensed from a container, formed a foam which collapsed in the ear canal faster than when the same foam was applied to the skin. It is thus disclosed that a foamable composition applied into the ear canal must form a foam having higher foam density than typical topical foams to prevent quick foam collapse and subsequent quick leaking out from the ear of the liquefied composition, as well as to enable administering therapeutic doses of the active agents into the small volume of the ear canal. Thus, the present invention provides foamable pharmaceutical compositions which form a foam having foam density higher than the foam density of commercially available topical foams, and as such are highly useful for otic administration.

The present invention now discloses that certain inactive ingredients should be avoided in order to produce a stable foam with the desired residence time in the ear. According to the principles of the present invention the foam will be sufficiently stable to remain within the ear for a minimum of at least one hour. According to the principles of the invention the foam collapses within one hour to three hours of administration of the foam into the ear canal. Thus, while short chain alcohols should be avoided as these alcohols accelerate foam collapse, white petrolatum is preferably present in the foamable compositions in order to stabilize the foam formed so as to obtain the desired foam collapse rate in the ear canal.

The foamable pharmaceutical compositions of the present invention comprise a small number of excipients, all of which are approved for otic and/or topical use. By virtue of the small number of excipients, the present invention discloses cost-effective otic foamable compositions. The compositions of the present invention produce a tolerable sensation and did not reduce significantly the hearing capability of human subjects treated with the compositions. Also, the foamable compositions of the present invention which comprise ciprofloxacin were found to be stable after long term storage, i.e., two years at room temperature, retaining the content of the quinolone antibiotic. As the foamable compositions of the present invention formed a stable foam in the ear canal, such foamable compositions provided extended exposure of the subject to the quinolone antibiotics, thereby enabled reducing the administration frequency of the quinolone antibiotics and hence prevented the exposure of the treated subject to higher doses of the antibiotics. Moreover, the foamable pharmaceutical composition of the present invention comprising ciprofloxacin as the sole active agent was found to cure subjects suffering from acute otitis externa at lower doses of the antibiotics as compared to commercially available ear drops which comprise both ciprofloxacin and dexamethasone. Thus, not only was it discovered that the foamable compositions of the present invention provided a dosage form of the quinolone antibiotics with improved compliance, but moreover such compositions improved the antibiotic efficacy in treating otitis externa and surprisingly avoided the need for use of a steroid anti-inflammatory agent.

The foamable pharmaceutical composition of the present invention is useful for treating external ear disorders and middle ear disorders. While dispensing the foam to the ear canal enables treating external ear disorders, dispensing the foam through a non-intact ear drum can enable treating middle ear disorders. The foamable compositions of the present invention therefore comprise inactive ingredients approved for external ear disorders as well as safe for middle ear disorders. It is accordingly disclosed that the foamable compositions of the present invention are devoid of propylene glycol as well as of other potentially ototoxic excipients.

According to a first aspect, the present invention provides a foamable otic pharmaceutical composition comprising:
(a) an oil-in-water emulsion comprising:
  (i) an antibiotic agent in an amount effective for antibacterial action;
  (ii) water in an amount of at least 75% (w/w);
  (iii) mineral oil in an amount of no more 15% (w/w);
  (iv) a synthetic surfactant pharmaceutically acceptable for otic application;
  (v) a foaming agent selected from a fatty alcohol and a fatty acid;
  (vi) white petrolatum; and
(b) a compressed propellant gas;
wherein the oil-in-water emulsion is devoid of organic polar co-solvents, the oil-in-water emulsion having osmolarity of about 280 mOsm/L to about 320 mOsm/L, and wherein the composition packaged in a container is adapted to form a foam after dispensing from the container.

It is to be understood that the foamable otic pharmaceutical composition of the present invention is stored as a liquid in an aerosol or pressurized container. Upon dispensing from the aerosol container, the foamable otic pharmaceutical composition forms foam suitable for application into the ear. Thus, the pharmaceutical composition of the present invention when administered to the ear of a subject, e.g., a human or an animal, is in the form of a foam.

According to some embodiments, water is present in the composition in an amount ranging from 82% to 88% (w/w)

of the total weight of the emulsion, alternatively in an amount ranging from 83% to 87% (w/w).

According to additional embodiments, mineral oil is present in the composition in an amount ranging from 7% to 10% (w/w) of the total weight of the emulsion. According to a certain embodiment, mineral oil is present in an amount of 9% to 10% (w/w).

According to some embodiments, the synthetic surfactant is selected from the group consisting of polysorbate 80, polysorbate 60, polysorbate 20, PEG-40 stearate, tyloxapol, and combinations thereof. Each possibility is a separate embodiment of the present invention. According to additional embodiments, the synthetic surfactant is polysorbate 80 present in an amount of about 1% to about 5% (w/w) of the total weight of the emulsion. According to further embodiments, the synthetic surfactant is PEG-40 stearate present in an amount of about 0.25% to about 2% (w/w) of the total weight of the emulsion. According to some embodiment, the surfactant is a mixture of polysorbate 80 and PEG-40 stearate present in an amount of about 1% to about 5% (w/w) and about 0.25% to about 2% (w/w), of the total weight of the emulsion, respectively. Alternatively, polysorbate 80 and PEG-40 stearate are present in the emulsion in an amount of about 3% to about 5% (w/w) and about 1% to about 2% (w/w), of the total weight of the emulsion, respectively. According to a certain embodiment, the surfactant is a mixture of polysorbate 80 and PEG-40 stearate present in an amount of 3% (w/w) and 1% (w/w) of the total weight of the emulsion, respectively.

According to still further embodiments, the foaming agent is a fatty alcohol or a fatty acid having at least 12 carbon atoms in the carbon chain. According to some embodiments, the foaming agent is selected from the group consisting of cetyl alcohol, stearyl alcohol, cetostearyl alcohol, stearic acid, and combinations thereof. Each possibility is a separate embodiment of the present invention. According to further embodiments, the foaming agent is present in an amount of about 0.25% to about 2% (w/w) of the total weight of the emulsion. According to a certain embodiment, the foaming agent is cetyl alcohol present in an amount of about 1% to about 2% (w/w) of the total weight of the emulsion. According to a certain embodiment, cetyl alcohol is present in an amount of about 1% (w/w). According to other embodiments, the foaming agent is cetostearyl alcohol, stearyl alcohol, or stearic acid present in an amount of about 0.25% to about 2% (w/w), alternatively in an amount of 0.5% to 1% (w/w) of the total weight of the emulsion.

According to yet further embodiment, white petrolatum is present in an amount that does not exceed 3% (w/w) of the total weight of the emulsion. According to certain embodiments, white petrolatum is present in an amount ranging from about 0.1% to about 1%, alternatively from 0.25% to 1% (w/w) of the total weight of the emulsion, further alternatively of 0.5% (w/w) of the total weight of the emulsion, thus providing the desired foam stability. It is to be understood that the present composition can comprise white petrolatum and/or an organic compound which can substitute while petrolatum, such organic compound is selected from the group consisting of alkanes, fatty acids, fatty acid alcohols, fatty acid esters, and alkyl ethers, and comprises at least eight carbon atoms. Said organic compound is characterized by being solid at 22° C., by having a melting point of at least 35° C., and by being approved for otic use.

According to some embodiments, the antibiotic agent is a quinolone antibiotic agent. According to additional embodiments, the quinolone antibiotic agent is selected from the group consisting of ciprofloxacin, ofloxacin, moxifloxacin, finafloxacin, besifloxacin, JNJ-Q2, levofloxacin, lomefloxacin, nadifloxacin, norfloxacin, pefloxacin, rufloxacin, balofloxacin, gatifloxacin, grepafloxacin, levofloxacin, pazufloxacin, sparfloxacin, temafloxacin, tosufloxacin, clinafloxacin, gemifloxacin, sitafloxacin, trovafloxacin, prulifloxacin, garenoxacin, delafloxacin, marbofloxacin, enrofloxacin, danofloxacin, difloxacin, ibafloxacin, orbifloxacin, sarafloxacin and salts thereof. Each possibility is a separate embodiment of the present invention. According to further embodiments, the quinolone antibiotic agent is selected from the group consisting of ciprofloxacin, ofloxacin, moxifloxacin, levofloxacin, marbofloxacin, enrofloxacin, finafloxacin, besifloxacin, JNJ-Q2, orbifloxacin, delafloxacin, pradofloxacin and salts thereof. According to a certain embodiment, the quinolone antibiotic is ciprofloxacin or a salt thereof. According to an exemplary embodiment, ciprofloxacin is ciprofloxacin hydrochloride. According to a further embodiment, the composition comprising a quinolone antibiotic is for animal use. According to an exemplary embodiment, the quinolone for animal use is marbofloxacin or enrofloxacin. The amount of the quinolone antibiotic ranges from 0.1% to 1% (w/w) of the total weight of the emulsion, alternatively from 0.3% to 0.5% (w/w) of the total weight of the emulsion. According to a certain embodiment, the quinolone antibiotic is ciprofloxacin hydrochloride present in an amount of 0.3% to 0.4% (w/w) of the total weight of the emulsion. According to an exemplary embodiment, ciprofloxacin hydrochloride is present in an amount of 0.35% (w/w) of the total weight of the emulsion).

According to further embodiments, the antibiotic agent is selected from the group consisting of aminoglycosides, ansamycins, carbacephems, carbapenems, cephalosporins, glycopeptides, lincosamides, lipopeptides, macrolides, monobactams, nitrofurans, oxazolidonones, penicillins, polypeptides, sulfonamides, and tetracyclines.

According to additional embodiments, the pharmaceutical composition can further comprise a steroid anti-inflammatory agent selected from the group consisting of dexamethasone, dexamethasone sodium phosphate, hydrocortisone, hydrocortisone acetate, prednisolone, methylprednisolone, prednisone, triamcinolone acetonide, mometasone, budesonide, fluocinolone acetonide, betamethasone, betamethasone sodium phosphate, betamethasone valerate, cortisone acetate, isoflupredone acetate, tixocortol pivalate, triamcinolone alcohol, amcinonide, desonide, fluocinonide, halcinonide, fluocortolone, hydrocortisone-17-butyrate, hydrocortisone-17-valerate, aclometasone dipropionate, betamethasone dipropionate, prednicarbate, clobetasone-17-butyrate,clobetasol-17-propionate, fluocortolone caproate, fluocortolone pivalate, and fluprednidene. Each possibility is a separate embodiment of the present invention. According to a certain embodiment, the steroid anti-inflammatory agent is dexamethasone. The anti-inflammatory steroid is present in the composition in an amount effective for anti-inflammatory action. Such amount typically ranges from 0.01% to 3% (w/w) of the total weight of the emulsion. According to a certain embodiment, the anti-inflammatory steroid is dexamethasone present in an amount of 0.1% (w/w) of the total weight of the emulsion.

According to yet further embodiments, the pharmaceutical composition further comprises a tonicity or an osmolarity adjusting agent. The tonicity or osmolarity adjusting agent is selected from the group consisting of salts e.g., sodium chloride, potassium chloride, and sugars, e.g., mannitol, dextrose, sorbitol. According to a certain embodiment, the tonicity agent is sodium chloride.

According to further embodiments, the pharmaceutical composition of the present invention further comprises at least one excipient selected from the group consisting of a preservative, a pH modifying agents, e.g., acetic acid and sodium hydroxide or a buffering system to achieve the desired pH, disodium edetate, and an antibacterial agent. According to another embodiment, the preservative is benzalkonium chloride. According to still further embodiment, the antibacterial agent is boric acid.

According to still further embodiments, the pH of the pharmaceutical composition ranges from about 4 to about 5. According to a certain embodiment, the pH of the pharmaceutical composition ranges from 4.3 to 4.8.

According to yet further embodiments, the propellant gas is volatile hydrocarbons such as butane, propane, isobutane, and mixture thereof. The amount of the compressed propellant gas in the pharmaceutical composition ranges from about 1% to about 8% by weight of the composition, alternatively from about 2% to about 6%, and further alternatively 4% by weight of the composition. It is to be understood that gas propellants such as, for example, hydrofluoroalkanes, chlorofluoroalkanes, dimethyl ethers, and methyl ethers can also be used as propellant gas in the compositions of the present invention.

According to yet further embodiments, the foamable otic pharmaceutical composition further comprises an analgesic agent or an anesthetic agent. Among the analgesic agents, antipyrine is preferred, and among the anesthetic agents, benzocaine, tetracaine, and procaine are preferred. Each possibility is a separate embodiment of the present invention.

According to still further embodiments, the composition is for animal use and further comprises an antifungal agent. Among the antifungal agents, nystatin, clotrimazole, miconazole, ketoconazole, fluconazole, thiabendazole, econazole, clomidazole, isoconazole, tioconazole, sulconazole, bifonazole, oxiconazole, fenticonazole, omoconazole, sertaconazole, flutrimazole, posaconazole can be used. Each possibility is a separate embodiment of the present invention. According to certain embodiments, nystatin, clotrimazole, miconazole, ketoconazole, fluconazole, and thiabendazole are preferred.

According to yet further embodiments, the foamable otic composition is for animal use and can further comprise an insecticide agent. Among the insecticide agents, pyrethrins, pyrethroids, piperonyl butoxide, and N-octyl bicycloheptene dicarboximide, or a combination thereof can be used. Each possibility is a separate embodiment of the present invention.

According to some embodiments, the foamable otic pharmaceutical composition comprises:
(a) an oil-in-water emulsion comprising:
  (i) ciprofloxacin HCl in an amount of 0.35% (w/w) of the total weight of the emulsion;
  (ii) water in an amount of 82% to 88% (w/w) of the total weight of the emulsion;
  (iii) mineral oil in an amount of 7% to 10% (w/w) of the total weight of the emulsion;
  (iv) a synthetic surfactant selected from the group consisting of polysorbate 80 in an amount of about 1% to about 5% (w/w), and PEG-40 stearate in an amount of 0.25% to about 2% (w/w) of the total weight of the emulsion;
  (v) cetyl alcohol in an amount of about 0.25% to about 2% (w/w) of the total weight of the emulsion;
  (vi) white petrolatum in an amount of about 0.1% to about 1% (w/w) of the total weight of the emulsion; and
(b) a compressed propellant gas in an amount of about 1% to about 8% (w/w) of the total weight of the composition;

According to additional embodiments, the foamable otic pharmaceutical composition comprises an oil-in-water emulsion comprising: ciprofloxacin HCl in an amount of 0.35% (w/w), water in an amount of 84% to 87% (w/w), mineral oil in an amount of 7% to 10% (w/w), polysorbate 80 in an amount of 3% to 5% (w/w), PEG-40 stearate in an amount of 1% to 2% (w/w), cetyl alcohol in an amount of 1% to 2% (w/w), white petrolatum in an amount of 0.25% to 0.5% (w/w) of the total weight of the emulsion, optionally further comprising at least one excipient selected from the group consisting of sodium chloride, benzalkonium chloride, disodium edetate, acetic acid, boric acid, and sodium hydroxide. According to an exemplary embodiment, the pharmaceutical composition can further comprise dexamethasone in an amount of about 0.1% (w/w) of the total weight of the emulsion.

According to additional embodiments, sodium choride is present in an amount of 0.5% (w/w), benzalkonium chloride is present in the composition in an amount of 0.01% (w/w), disodium edetate is present in an amount of 0.1% (w/w), acetic acid is present in an amount of 0.1% (w/w), boric acid is present in an amount of 0.01% to 0.04% (w/w) of the total weight of the emulsion, and sodium hydroxide is present in an amount to achieve a pH of the pharmaceutical composition of about 4 to about 5 before adding the compressed propellant gas.

According to a certain embodiment, the oil-in-water emulsion comprises:

| Ingredient | % (w/w) |
| --- | --- |
| Water | 84.3 |
| Mineral oil | 9 |
| Polysorbate 80 (Tween 80) | 3 |
| PEG-40 stearate | 1 |
| Cetyl alcohol | 1 |
| White petrolatum | 0.5 |
| Acetic acid | 0.1 |
| NaOH | 0.025 |
| EDTA (disodium edetate) | 0.1 |
| Benzalkonium chloride | 0.01 |
| Boric acid | 0.03 |
| NaCl | 0.5 |
| Ciprofloxacin Hydrochloride | 0.35 |

According to another embodiment, the oil-in-water emulsion comprises:

| Ingredient | % (w/w) |
| --- | --- |
| Water | 86.5 |
| Mineral oil | 7 |
| Polysorbate 80 (Tween 80) | 3 |
| PEG-40 stearate | 1 |
| Cetyl alcohol | 1 |
| White petrolatum | 0.25 |
| Acetic acid | 0.1 |
| NaOH | 0.025 |
| EDTA (disodium edetate) | 0.1 |
| Benzalkonium chloride | 0.01 |
| Boric acid | 0.03 |
| NaCl | 0.5 |
| Ciprofloxacin Hydrochloride | 0.35 |
| Dexamethasone | 0.1 |

According to a further aspect, the present invention provides a method for treating an ear disorder comprising administering to the ear canal of a subject in need of such treatment a therapeutically effective amount of the foamable otic pharmaceutical composition according to the principles of the present invention.

According to some embodiments, the subject is a human. According to additional embodiments, the subject is an animal. According to further embodiments, the animal is a domestic pet animal. According to certain embodiments, the domestic pet animal is a dog or a cat.

According to additional embodiments, the ear disorder is selected from the group consisting of external ear disorder, middle ear disorder and inner ear disorder. Each possibility is a separate embodiment of the present invention. According to a certain embodiment, the ear disorder is otitis externa (swimmer's ear). According to another embodiment, the ear disorder is otitis media. According to additional embodiment, the otitis externa is acute otitis externa. According to a further embodiment, the otitis externa is chronic otitis externa. According to further embodiments, the otitis media is selected from the group consisting of chronic suppurative otitis media and serous or secretory otitis media due to tympanostomy tubes. Each possibility is a separate embodiment of the present invention.

According to yet further aspect, the present invention provides a foamable pharmaceutical composition for treating an ear disorder, the pharmaceutical composition comprises: (a) an oil-in-water emulsion comprising: (i) an antibiotic agent in an amount effective for antibacterial action; (ii) water in an amount of at least 75% (w/w); (iii) mineral oil in an amount of no more than 15% (w/w); (iv) a synthetic surfactant pharmaceutically acceptable for otic use; (v) a foaming agent selected from a fatty alcohol and a fatty acid; (vi) white petrolatum; and (b) a compressed propellant gas; wherein the oil-in-water emulsion is devoid of organic polar co-solvents, the oil-in-water emulsion having osmolarity of about 280 mOsm/L to about 320 mOsm/L, and wherein the oil-in-water emulsion and the compressed propellant gas packaged in a container being adapted to form a foam after dispensing from the container according to the principles of the present invention.

These and other embodiments of the present invention will be better understood in relation to the description, examples and claims that follow.

BRIEF DESCRIPTION OF THE FIGURES

FIG. 1 shows a Kaplan-Meier survival curve of the estimated time-to-end of pain in Ciprodex® and FoamOtic treated subjects.

DETAILED DESCRIPTION OF THE INVENTION

The present invention provides a foamable otic pharmaceutical composition comprising: (a) an oil-in-water emulsion comprising: (i) an antibiotic agent or a salt thereof in an amount effective for antibacterial action; (ii) water in an amount of at least 75% (w/w); (iii) mineral oil in an amount of no more than 15% (w/w); (iv) a synthetic surfactant pharmaceutically acceptable for otic application; (v) a foaming agent; (vi) white petrolatum; and (b) a compressed propellant gas; wherein the emulsion is devoid of organic polar co-solvents, the oil-in-water emulsion having osmolarity of about 280 mOsm/L to about 320 mOsm/L, and wherein the composition being packaged in a container is adapted to form stable foam after dispensing from the container.

It is now disclosed that short chain alcohols accelerated foam collapse. It is further disclosed that cellulose derivatives, such as hydroxyethyl cellulose, as well as the emulsifier lecithin increased the tackiness of some compositions. The foamable composition of the present invention is therefore devoid of short chain alcohols, and according to a certain embodiment the composition is devoid of gelling agents, such as cellulose derivatives. According to additional embodiment, the composition is devoid of lecithin. It is further disclosed that glycerin monostearate (GMS) was ineffective in stabilizing the foam. Thus, the composition is devoid of GMS and other organic polar co-solvents such as propylene glycol.

It is further disclosed that the amounts of the excipients affected the emulsion stability as well as the foam quality and the foam collapse rate. Thus, 1% (w/w) of the synthetic surfactant polysorbate 80 was not as effective as 3% or 5% (w/w) of the surfactant in stabilizing the emulsion and in improving foam quality.

The foaming agent cetyl alcohol in amounts of 0.25% and 0.5% (w/w) was not as effective in stabilizing the emulsion and in attenuating foam collapse as 1% to 2% (w/w) which were shown to stabilize both the emulsion and the foam.

The synthetic surfactant PEG-40 stearate in amounts of 0.25% and 0.5% was not as effective as 1% to 2% (w/w) in stabilizing the emulsion or in attenuating foam collapse.

Mineral oil was found to improve foam quality and to stabilize the foam in amounts of 9% or 10% (w/w), while lower concentrations, e.g., 7% or 8%, were found to be less effective.

White petrolatum in the amount of 1% (w/w) significantly attenuated foam collapse, 0.5% and 0.25% (w/w) have a milder effect on the foam collapse rate. Thus, the foamable pharmaceutical compositions of the present invention require certain excipients at a narrow concentration range so as to enable obtaining stable oil-in-water emulsions and stable foam which collapses in the ear canal within one hour to three hours post administration.

The present invention provides foamable otic pharmaceutical compositions for use in treating ear disorders in humans and in animals. It is to be understood that the compositions for animal use can further comprise anti-fungal agents and/or miticide agents.

The term "emulsion" describes a dosage form consisting of a two-phase system comprised of at least two immiscible liquids, one of which is dispersed as droplets (internal or dispersed phase) within the other liquid (external or continuous phase) generally stabilized with one or more surfactants or emulsifying agents. Oil-in-water emulsion denotes an emulsion where the oil is the dispersed phase, and water is the external or continuous phase.

The term "devoid" as used herein denotes an amount of an excipient which is present in an amount of less than 0.1% (w/w) of the emulsion, preferably of less than about 0.05% (w/w), and more preferably it is absent. In reference to polar co-solvents, the term "devoid" denotes an amount of less than 5% (w/w), preferably of less than 3% (w/w) or less than 2% (w/w), more preferably of less than 1% (w/w) of the total weight of the emulsion, and most preferably the polar co-solvents are absent.

The term "foam collapse rate" denotes the kinetics of foam coarsening and destruction resulting from the rupture of bubbles or from gas transfer from small to large bubbles and bubble coalescence occurring within the ear of a subject or within a tube.

The term "foam quality" denotes the appearance of the foam which is graded from rich and creamy appearance (++++) to barely foamy, not creamy appearance (+).

The term "stable emulsion" denotes a homogenous emulsion having essentially no irreversible separation of the two phases.

The term "about" as used herein denotes ±10% of the value indicated.

The term "polar co-solvent" refers to an organic co-solvent, typically soluble in both water and oil. Examples of polar co-solvents include polyols, such as glycerol (glycerin), propylene glycol, hexylene glycol, diethylene glycol, propylene glycol n-alkanols, and the like.

The term "therapeutically effective amount" is that amount of an active agent which is sufficient to provide a beneficial effect to the subject to which the active agent is administered. More specifically, a therapeutically effective amount means an amount of a quinolone antibiotic and/or a steroid anti-inflammatory agent effective to alleviate or ameliorate the symptoms of an ear disorder of the subject being treated. When otitis externa is treated, ear edema, ear pain, ear discharge, and tenderness to movement of the tragus/pinna are typical symptoms.

It is to be appreciated that the foamable composition of the present invention comprises water in an amount of 82% to 88% (w/w) of the total weight of the emulsion. Alternatively the foamable composition comprises between 83% and 87% (w/w) of the total weight of the emulsion, or between 84% to 85% (w/w) of the total weight of the emulsion.

The compositions of the present invention comprise a mineral oil. Mineral oil (e.g., Chemical Abstracts Service Registry number 8012-95-1) is a mixture of aliphatic, naphthalenic, and aromatic liquid hydrocarbons that derive from petroleum.

The terms "surfactant" or a "surface-active agent" include any agent linking oil and water in the composition, in the form of emulsion. A hydrophilic/lipophilic balance (HLB) of a surfactant indicates its affinity toward water or oil. The HLB scale ranges from 1 (totally lipophilic) to 20 (totally hydrophilic), with 10 representing an equal balance of both characteristics. Hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average).

According to some embodiments of the present invention, the surfactant has a hydrophilic lipophilic balance (HLB) between about 9 and about 14, which is the required HLB (the HLB required to stabilize an O/W emulsion of a given oil) of most oils and hydrophobic solvents. Thus, in one or more embodiments, the composition contains a single surface active agent having an HLB value between about 9 and 14, and in one or more embodiments, the composition contains more than one surface active agents and the weighted average of their HLB values is between about 9 and about 14. Non-limiting examples of possible surfactants include polysorbates, such as polyoxyethylene sorbitan monolaurate (polysorbate 20), polyoxyethylene sorbitan monostearate (polysorbate 60) and polyoxyethylene sorbitan monooleate (polysorbate 80); tyloxapol; glyceryl stearate; PEG-40 stearate; polyoxyethylene (POE) fatty acid esters; poly(oxyethylene) alkylyl ethers, such as poly(oxyethylene) cetyl ether, poly(oxyethylene) palmityl ether, polyethylene oxide hexadecyl ether, polyethylene glycol cetyl ether, and the like, and a combination thereof.

The composition of the present invention further comprises a foaming agent which can also act as an emulsifier as known in the art. It is to be understood that the foaming agent enables obtaining foam with the desired collapse rate. The foaming agent can be a fatty alcohol having 12 or more carbons in its carbon chain, such as lauryl alcohol, myristyl alcohol, cetyl alcohol, stearyl alcohol, cytostearyl alcohol, oleyl alcohol, and linoleyl alcohol, or mixtures thereof. Other examples of fatty alcohols are arachidyl alcohol (C20), behenyl alcohol (C22), 1-triacontanol (C30), as well as alcohols with longer carbon chains (up to C50).

According to further embodiments, the antibiotic agent is a quinolone antibiotic. According to additional embodiments, the antibiotic agent is selected from the group consisting of aminoglycosides such as amikacin, gentamicin, kanamycin, neomycin, netilmicin, tobramycin, paromomycin, spectinomycin and the like; ansamycins such as geldanamycin, herbimycin, rifaximin, streptomycin; carbacephems such as loracarbef; carbapenems such as ertapenem, doripenem, imipenem/cilastatin, meropenem; cephalosporins such as cefadroxil, cefazolin, cefalotin or cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, ceftaroline fosamil, ceftobiprole; glycopeptides such as teicoplanin, vancomycin, telavancin; lincosamides such as clindamycin, lincomycin; lipopeptides such as daptomycin; macrolides such as azithromycin, clarithromycin, dirithromycin, erythromycin, roxithromycin, troleandomycin, telithromycin, spiramycin; monobactams such as aztreonam; nitrofurans such as furazolidone, nitrofurantoin; oxazolidonones such as linezolid, posizolid, radezolid, torezolid; penicillins such as amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, temocillin, ticarcillin and combination of penicillins with clavulanic acid; polypeptides such as bacitracin, colistin, polymyxin b; sulfonamides such as mafenide, sulfacetamide, sulfadiazine, silver sulfadiazine, sulfadimethoxine, sulfamethizole, sulfamethoxazole, sulfasalazine, sulfisoxazole, trimethoprim-sulfamethoxazole; tetracyclines such as tetracycline, demeclocycline, doxycycline, minocycline, oxytetracycline; arsphenamine, chloramphenicol, fosfomycin, fusidic acid, metronidazole, mupirocin, platensimycin, quinupristin/dalfopristin, thiamphenicol, tigecycline, tinidazole, and trimethoprim, or a combination thereof.

The "gelling agent" as referred to is defined as a naturally-occurring polymeric material, a semi-synthetic polymeric material, or a synthetic polymeric material useful as thickeners to provide higher viscosity of the composition than that of water. The naturally-occurring polymeric materials include, for example, locust bean gum, sodium alginate, sodium caseinate, egg albumin, gelatin agar, carrageenan gum sodium alginate, xanthan gum, quince seed extract, tragacanth gum, starch, chemically modified starches and the like. The semi-synthetic polymeric materials include, for example, cellulose ethers (e.g. hydroxyethyl cellulose, methyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like. The synthetic polymeric materials include, for example, carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers and the like.

The compositions of the present invention can be subjected to nano-sizing. Methods for nano-sizing of compositions are well known in the art and include, but not limited to, nano-sizing by a high pressure homogenizer.

The composition of the present invention can further comprise a variety of formulation excipients. Such excipients can be selected, for example, from preservatives (e.g., benzalkonium chloride or benzyl alcohol); pH modifying agents such as acid and base (e.g., acetic acid and sodium hydroxide, and the like) or buffering agents to obtain the desired pH; tonicity agents (e.g., salts such sodium chloride); antibacterial agents (e.g., boric acid or zinc); disodium edetate; anti-oxidants (e.g., □-tocopherol or a salt thereof, butylated hydroxytoluente, and the like); and other formulation components used in the art of formulations.

Gas propellants are used to generate and administer the foamable composition as foam. Examples of suitable gas propellants include volatile hydrocarbons such as butane, propane, isobutane or mixtures thereof, and fluorocarbon gases. The amount of the compressed propellant or liquefied gas is adapted to provide foam collapse within about 30 minutes to about 2 hours after administration of the foam into the ear of a subject. The amount of the compressed propellant gas is adapted to provide foam density of about 0.05 gr/ml to about 0.15 gr/ml, alternatively from about 0.07 gr/ml to about 0.11 gr/ml, further alternatively from 0.07 gr/ml to 0.09 gr/ml.

The compositions of the present invention can be used for treating external ear disorders, middle ear disorders and inner ear disorders. Each possibility is a separate embodiment of the present invention. External ear disorders include, but are not limited to, otitis externa including acute otitis externa and chronic otitis externa, blockage of the ear canal, otomycosis, granular myringitis, perichondritis, and bullous myringitis. Each possibility is a separate embodiment of the present invention. Middle ear disorders include, but are not limited to, otitis media including serous otitis media and chronic otitis media, mastoiditis, ruptured ear drum, and myringitis. Each possibility is a separate embodiment of the present invention. Inner ear disorders include, but are not limited to, Meniere's disease and tinnitus. Each possibility is a separate embodiment of the present invention.

EXAMPLE 1

Foam Formulations and Characterization

The different foam formulations were evaluated for foam quality, pH, appearance after centrifugation, foam density, foam collapse rate in vitro and in vivo, and sensory assessment of the foam in the ear as follows:

Foam Quality:

Visual inspection used to characterize the grade of the resulting foam was as follows:
Excellent (++++)—very rich and creamy in appearance;
Very good (+++)—rich and creamy in appearance.
Good (++)—rich and creamy in appearance, but have large bubble structure;
Poor (+)—barely foamy, not creamy, liquid in appearance.

pH:

The pH was determined during the formulation preparation process and at the foam level. The pH was also measured at different time points during the accelerated stability studies.

Centrifugation Test:

The test was aimed at assessing the emulsion stability at accelerated conditions. High speed centrifugation was used to mimic the phase separation process that would occur as a result of time. The test was performed as follows: About 1 gr of emulsion formulation was weighed and spun in a microfuge tube for 10 minutes at 3,000 RPM (equivalent to X600 g) or at 10,000 RPM (equivalent to X6700 g). The formulation appearance was graded according to the degree of phase separation as follows:

Creaming (Cr.)—Upper layer-opaque, Lower layer-transparent or translucent, reversible situation [% Creaming describes the percentage that occupies the upper layer portion]: Grade ++++ is equivalent to 90%-100% creaming (negligible separation). Grade +++ is equivalent to 60%-90% creaming. Grade ++ is equivalent to 30%-60% creaming. Grade + is equivalent to up to 30% creaming (significant separation).

Foam Density:

Foam was released from the pressurized canister into a pre-weighed graduated cylinder and foam was allowed to expand to its maximal volume. The weight and the volume of the foam were recorded. Foam density was defined as the weight recorded divided by the final volume after foam expansion. The test was performed and recorded 3 times independently.

Foam Collapse Rate in Vitro:

Foam collapse rate in vitro was determined by delivering the foamable composition into a transparent glass tube. The glass tube was pre-warmed and maintained at 40° C. for up to two hours. At different time points the remaining foam volume was assessed visually and expressed at percentage of the initial volume.

Foam Collapse Rate in Vivo:

Foam was introduced in the ear canal of healthy adult human subjects and the time of application was recorded. The percentage of the remaining foam was assessed at different time points for up to 3 hours. The subjects were allowed to continue their normal activities during the study.

Analytical Determination of Ciprofloxacin and Dexamethasone in the Formulations:

To determine the amount of ciprofloxacin or dexamethasone present in the foam formulations, an Ultra Performance Liquid Chromatography (UPLC) based method was used to test the emulsions (devoid of propellant) designated herein below bulk formula or bulk emulsion as well as the foam formulations which contained the propellant.

Foam Development:

Table 1 lists the excipients used for formulation development.

TABLE 1

Formulation excipients.

| Excipient | Role in formulation |
| --- | --- |
| Oil phase | |
| Mineral oil | Oil, emollient |
| Cetyl alcohol | Foaming agent, emulsifier |
| Cetostearyl alchol | Foaming agent, emulsifier |
| Stearyl alcohol | Foaming agent, emulsifier |
| Stearic acid | Foaming agent, emulsifier |
| PEG-40 stearate | Surfactant |
| Water phase | |
| Water | Solvent |
| Polysorbate 80 | Surfactant |
| Acetic acid | pH modifying agent |

TABLE 1-continued

Formulation excipients.

| Excipient | Role in formulation |
|---|---|
| Benzalkonium chloride | Preservative |
| Sodium hydroxide | pH modifying agent |
| Sodium chloride | Tonicity agent |
| Disodium EDTA | |
| Boric acid | |
| Propane, Butane, Isobutane | Propellant |

Preparation of Foamable Formulations
5. Water Phase
   Acetic acid, NaOH, EDTA, Boric acid, NaCl, benzalkonium chloride, and Polysorbate 80 were added to water and stirred on a hot plate while heating to 70° C. until a clear solution was obtained.
   Ciprofloxacin HCl was then added and stirred for 5 minutes at 70° C.
6. Oil Phase
   Mineral oil, PEG 40 stearate, cetyl alcohol and white petrolatum were stirred on a hot plate while heating to 70° C. until a clear phase was obtained (5-10 minutes).
7. Emulsification/Homogenization
   The oil phase was added to the water phase while homogenizing using a Kinematica Polytron homogenizer (Model PT10-35). The homogenizing continued for additional 3 minutes (for 2 kg emulsion). Thereafter, the emulsion was mixed at 450 rpm, then at 300 rpm at room temperature with impeller (stirrer diameter 6.5 cm, shaft length 32 cm). The pH was determined and adjusted as needed. The emulsion was weighted and water was added if needed.
8. Packaging Procedure
   Canisters and valves were washed with ethanol and filled with 12±1 gr of the emulsion. The valves were crimped on the canister. Hydrocarbon propellant mixture (0.48±0.1 gr; 4% w/w of the final formulation) was added.

Results

Three formulations were initially prepared and are presented in Table 2.

TABLE 2

Formulations #62, 65 and 67.

| Ingredient | Formulation #62 (%) | Formulation #65 (%) | Formulation #67 (%) |
|---|---|---|---|
| Ciprofloxacin HCl | 0.35 | 0.35 | 0.35 |
| Dexamethasone | 0.1 | 0.1 | 0.1 |
| Water | 85 | 85 | 86 |
| Mineral oil | 7 | 7 | 7 |
| Polysorbate 80 | 3 | 2.4 | 2.4 |
| PEG-40 stearate | 0.5 | 1 | 0.5 |
| Cetyl alcohol | 1 | 1 | 0.5 |
| Acetic acid | 0.1 | 0.1 | 0.1 |
| Sodium hydroxide | 0.025 | 0.025 | 0.025 |
| EDTA | 0.1 | 0.1 | 0.1 |
| Benzalkonium chloride | 0.02 | 0.02 | 0.02 |
| Boric acid | 0.04 | 0.04 | 0.04 |
| Sodium chloride | 0.1 | 0.1 | 0.1 |

Formulations #62 and #65 resulted in foam which collapsed within 20 minutes after dispensing to a tube at 40° C. or to the ear canal, dripping out from the ear once collapsed. Formulation #67 resulted in foam which collapsed even faster, i.e., within few minutes in a tube at 40° C. and in the ear canal. As the amount of cetyl alcohol in formulation #67 was half the amount in formulations #62 and #65, the results indicated that the amount of cetyl alcohol should be of about 1% (w/w) to obtain stable foam.

In the course of developing foamable compositions which form stable foam in the ear canal, various excipients such as while petrolatum, glycerol, glycerin monostearate, lecithin, and hydroxyethyl cellulose (HEC) have been added to the compositions.

TABLE 3

Formulations #32, 36, 38, 40 and 77.

| Ingredient | #32 % (w/w) | #36 % (w/w) | #38 % (w/w) | #40 % (w/w) | #77 % (w/w) |
|---|---|---|---|---|---|
| Water | 78 | 77.8 | 77.85 | 87.95 | 87.5 |
| Mineral oil | 5 | 5 | 5 | 5 | 7 |
| Polysorbate 80 | 3 | 3 | 3 | 3 | 3 |
| PEG-40 stearate | 1 | 1 | 1 | 1 | 1 |
| Cetyl alcohol | 1 | 1 | 1 | 1 | 1 |
| White petrolatum | 2 | 2 | 2 | 2 | |
| Glycerol | 10 | 10 | 10 | | |
| Glycerin monostearate | | 0.2 | | | |
| Lecithin | | | 0.15 | | |
| Citric acid | | | | 0.05 | |
| Hydroxyethylcellulose | | | | | 0.1 |

Formulation #36 to which glycerin monostearate (GMS) was added in order to increase foam consistency did not form stable foam as it collapsed within few minutes. Formulations #38 and #77 to which lecithin or HEC were added, respectively, were sticky. Formulation #40 to which citric acid was added resulted in foam that collapsed within few minutes.

In order to stabilize the foam, the presence of PEG-40 stearate was evaluated.

TABLE 4

Formulations #57, 58, 61 and 62.

| Ingredient | #57 | #58 | #61 | #62 |
|---|---|---|---|---|
| Water | 82.5 | 84.5 | 85.5 | 85 |
| Min. Oil | 7 | 7 | 7 | 7 |
| Polysorbate 80 | 3 | 3 | 3 | 3 |
| PEG-40-stearate | 1 | 1 | 0 | 0.5 |
| Cetyl Alcohol | 1 | 1 | 1 | 1 |
| White Petrolatum | 2 | 0 | 0 | 0 |
| Glycerin | 0 | 0 | 0 | 0 |
| Acetic Acid | 0.1 | 0.1 | 0.1 | 0.1 |
| NaOH | 0.025 | 0.025 | 0.025 | 0.025 |
| EDTA | 0.01 | 0.01 | 0.01 | 0.1 |
| BAC | 0.01 | 0.01 | 0.01 | 0.01 |
| Boric Acid | 0.03 | 0.03 | 0.03 | 0.03 |
| Ciprofloxacin | 0.35 | 0.35 | 0.35 | 0.35 |
| Dexamethasone | 0.1 | 0.1 | 0.1 | 0.1 |
| NaCl | 0.9 | 0.9 | 0.9 | 0.9 |

Formulations #57 and 58 listed in Table 4 were found to form a stable foam under in-vitro conditions while formulation #61 formed a foam that collapsed quickly (quick-breaking) under these conditions. The results indicated that PEG-40 Stearate is essential for foam stability. Formulation #62 formed a stable foam yet when applied into the ear it collapsed within approximately 10 minutes and a fraction of the formulation dripped out of the ear.

Further experiments were performed aiming at developing foamable compositions which show foam collapse 60 minutes after dispensing from a container into the ear and which do not drain out of the ear canal once liquefied.

TABLE 5

Formulations #104, 109, 111 and 112.

| Ingredient | #104 % (w/w) | #109 % (w/w) | #111 % (w/w) | #112 % (w/w) |
|---|---|---|---|---|
| Water | 85.8 | 86.3 | 86.5 | 86.5 |
| Mineral oil | 7 | 7 | 7 | 7 |
| Polysorbate 80 | 3 | 3 | 3 | 3 |
| PEG-40 stearate | 1 | 1 | 1 | 1 |
| Cetyl alcohol | 1 | 1 | 1 | 1 |
| White petrolatum | 1 | 0.5 | 0.25 | 0.1 |
| Acetic acid | 0.1 | 0.1 | 0.1 | 0.1 |
| NaOH | 0.025 | 0.025 | 0.025 | 0.025 |
| EDTA (disodium edetate) | 0.1 | 0.1 | 0.1 | 0.1 |
| Benzalkonium chloride | 0.01 | 0.01 | 0.01 | 0.01 |
| Boric acid | 0.03 | 0.03 | 0.03 | 0.03 |
| NaCl | 0.9 | 0.9 | 0.9 | 0.9 |
| Ciprofloxacin HCl | 0.35 | 0.35 | 0.35 | 0.35 |
| Dexamethasone | 0.1 | 0.1 | 0.1 | 0.1 |

Formulation #104 which contained 1% white petrolatum (w/w) of the total weight of the emulsion formed stable foam that showed minor collapse in the ear three hours after dispensing from the container. In contrast, formulation #112 which contained 0.1% (w/w) white petrolatum, collapsed within 30 to 60 minutes after dispensing from the container. Formulations #109 and #111 were found to show the desired foam stability, namely they showed significant collapse in the ear canal 60 to 120 minutes after dispensing.

EXAMPLE 2

Optimization of Formulation Excipients

Adjustment of Osmolarity

In order to achieve the required osmolarity (~300 mOsm/L), increasing amounts of sodium chloride were added to formula #62 (prepared in the absence of sodium chloride). The osmolarity of the formulae was measured using the Advanced® Model 3300 Osmometer. The results indicated that addition of sodium chloride at a final concentration of 0.5% w/w to formula #62 increased the osmolarity from 91 mOsm/L to 285 mOsm/L. It was further demonstrated that addition of 0.25% w/w of white petrolatum increased the osmolarity by 15 mOsm/L. Therefore, formulae comprising 0.5% w/w sodium chloride and up to 0.5% w/w white petrolatum are within the acceptable range of osmolarity.

Adjustment of Polysorbate 80

Optimization of Polysorbate 80 was performed on formulation #109.

TABLE 6

Formulation #109 with increasing amounts of polysorbate 80.

| Ingredients | #109 Polysorbate 80 (1%) % (w/w) | #109-Control Polysorbate 80 (3%) % (w/w) | #109 Polysorbate 80 (5%) % (w/w) |
|---|---|---|---|
| Water | 88.735 | 86.735 | 84.735 |
| Mineral Oil | 7 | 7 | 7 |
| Polysorbate 80 | 1 | 3 | 5 |
| PEG-40 stearate | 1 | 1 | 1 |
| Cetyl Alcohol | 1 | 1 | 1 |
| White Petrolatum | 0.5 | 0.5 | 0.5 |
| Acetic Acid | 0.1 | 0.1 | 0.1 |
| NaOH | 0.025 | 0.025 | 0.025 |
| EDTA | 0.1 | 0.1 | 0.1 |
| Benzalkonium Chloride | 0.01 | 0.01 | 0.01 |

TABLE 6-continued

Formulation #109 with increasing amounts of polysorbate 80.

| Ingredients | #109 Polysorbate 80 (1%) % (w/w) | #109-Control Polysorbate 80 (3%) % (w/w) | #109 Polysorbate 80 (5%) % (w/w) |
|---|---|---|---|
| Boric Acid | 0.03 | 0.03 | 0.03 |
| NaCl | 0.5 | 0.5 | 0.5 |
| Total | 100 | 100 | 100 |

TABLE 7

Foam characteristics of the formulations of Table 6.

| | | | |
|---|---|---|---|
| Separation of bulk formula-upon storage at 25° C. for 7 days | +++ | ++++ | ++++ |
| Separation of bulk formula-upon storage at 40° C. for 7 days | +++ | ++++ | ++++ |
| Centrifugation results 3,000 RPM | ++++ | +++ | +++ |
| Centrifugation results 10,000 RPM | +++ | ++ | +++ |
| Foam quality | +++ | ++++ | ++++ |
| Foam collapse after storage at 5° C. for 7 days | ++++ | ++++ | +++ |
| Foam collapse after storage at room temp for 7 days | ++++ | ++++ | ++++ |
| Foam collapse after storage at 40° C. for 7 days | ++++ | ++++ | ++++ |

As shown in Table 7, foam quality was reduced when the amount of polysorbate 80 was reduced to 1% (w/w) of the emulsion. In addition, the formulation which contained 1% polysorbate 80 showed higher separation than that of formulations having higher amounts of polysorbate 80. No advantage was found when increasing the amount of polysorbate 80 from 3% to 5% (w/w of the total weight of the emulsion).

Adjustment of Cetyl Alcohol

To optimize the amount of cetyl alcohol, formulation #109 was prepared with 0.25% to 1% (w/w) of cetyl alcohol.

TABLE 8

Formulation #109 with increasing amounts of cetyl alcohol.

| Ingredients | #109 Cetyl Alcohol 0.25% % (w/w) | #109 Cetyl Alcohol 0.5% % (w/w) | #109-Control-Cetyl Alcohol % (w/w) | #109 Cetyl Alcohol 2.0% % (w/w) |
|---|---|---|---|---|
| Water | 87.485 | 87.235 | 86.735 | 85.735 |
| Mineral Oil | 7 | 7 | 7 | 7 |
| Polysorbate 80 | 3 | 3 | 3 | 3 |
| PEG-40 stearate | 1 | 1 | 1 | 1 |
| Cetyl Alcohol | 0.25 | 0.5 | 1 | 2 |
| White Petrolatum | 0.5 | 0.5 | 0.5 | 0.5 |
| Acetic Acid | 0.1 | 0.1 | 0.1 | 0.1 |
| NaOH | 0.025 | 0.025 | 0.025 | 0.025 |
| EDTA | 0.1 | 0.1 | 0.1 | 0.1 |
| Benzalkonium Chloride | 0.01 | 0.01 | 0.01 | 0.01 |
| Boric Acid | 0.03 | 0.03 | 0.03 | 0.03 |
| NaCl | 0.5 | 0.5 | 0.5 | 0.5 |
| Total | 100 | 100 | 100 | 100 |

TABLE 9

Foam characteristics of the formulations of Table 8.

| | | | | |
|---|---|---|---|---|
| Separation of bulk formula—upon storage at 25° C. for 7 days | + | ++ | ++++ | ++++ |
| Separation of bulk formula—upon storage at 40° C. for 7 days | + | + | ++++ | ++++ |
| Centrifugation results 3,000 RPM | + | +++ | +++ | ++++ |
| Centrifugation results 10,000 RPM | + | ++ | ++ | ++++ |
| Foam quality | ++++ | ++++ | ++++ | ++++ |
| Foam collapse after storage at 5° C. for 7 days | + | +++ | ++++ | ++++ |
| Foam collapse after storage at room temp for 7 days | + | ++++ | ++++ | ++++ |
| Foam collapse after storage at 40° C. for 7 days | + | ++++ | ++++ | ++++ |

As shown in Table 9, foam collapse was accelerated when the amount of cetyl alcohol was reduced to 0.25% or 0.5% (w/w of the total weight of the emulsion). In addition, the formulations having 0.25% or 0.5% (w/w) of cetyl alcohol showed higher separation compared to formulations having higher amounts of cetyl alcohol. Increasing the amount of cetyl alcohol from 1% to 2% (w/w) did not have a significant effect on foam stability.

Adjustment of PEG-40 Stearate

TABLE 10

Formulation #109 with increasing amounts of PEG-40 stearate.

| Ingredients | #109 PEG-40 stearate 0.25% % (w/w) | #109 PEG-40 stearate 0.5% % (w/w) | #109-Control-PEG-40 Stearate 1% % (w/w) | #109 PEG-40 stearate 2% % (w/w) |
|---|---|---|---|---|
| Water | 87.485 | 87.235 | 86.735 | 85.735 |
| Mineral Oil | 7 | 7 | 7 | 7 |
| Polysorbate 80 | 3 | 3 | 3 | 3 |
| PEG-40 stearate | 0.25 | 0.5 | 1 | 2 |
| Cetyl Alcohol | 1 | 1 | 1 | 1 |
| White Petrolatum | 0.5 | 0.5 | 0.5 | 0.5 |
| Acetic Acid | 0.1 | 0.1 | 0.1 | 0.1 |
| NaOH | 0.025 | 0.025 | 0.025 | 0.025 |
| EDTA | 0.1 | 0.1 | 0.1 | 0.1 |
| Benzalkonium Chloride | 0.01 | 0.01 | 0.01 | 0.01 |
| Boric Acid | 0.03 | 0.03 | 0.03 | 0.03 |
| NaCl | 0.5 | 0.5 | 0.5 | 0.5 |
| Total | 100 | 100 | 100 | 100 |

TABLE 11

Foam characteristics of the formulations of Table 10.

| | | | | |
|---|---|---|---|---|
| Separation of bulk formula—upon storage at 25° C. for 7 days | ++++ | ++++ | ++++ | ++++ |
| Separation of bulk formula—upon storage at 40° C. for 7 days | ++++ | ++++ | ++++ | ++++ |
| Centrifugation results 3,000 RPM | ++++ | ++++ | +++ | ++++ |
| Centrifugation results 10,000 RPM | +++ | ++ | ++ | + |
| Foam quality | ++++ | ++++ | ++++ | ++++ |
| Foam collapse after storage at 5° C. for 7 days | ++ | +++ | ++++ | ++++ |
| Foam collapse after storage at room temp for 7 days | ++++ | ++++ | ++++ | ++++ |
| Foam collapse after storage at 40° C. for 7 days | ++++ | ++++ | ++++ | ++++ |

As shown in Table 11, foam collapse of the formulations stored at 5° C. for 1 week was accelerated when the amount of PEG-40 stearate was reduced to 0.25% and 0.5% (w/w of the total weight of the emulsion). Based on the results of the centrifugation assay, increasing the amount of PEG-40 stearate to 2% (w/w) increased the separation of the formulation.

Adjustment of the Concentration of Mineral Oil Formula

TABLE 12

Formulation #109 with increasing amounts of mineral oil.

| Ingredients | #109-Control Mineral oil 7% % (w/w) | #109 Mineral oil 8% % (w/w) | #109 Mineral oil 9% % (w/w) | #109 Mineral oil 10% % (w/w) |
|---|---|---|---|---|
| Water | 86.735 | 85.735 | 84.735 | 83.735 |
| Mineral Oil | 7 | 8 | 9 | 10 |
| Polysorbate 80 | 3 | 3 | 3 | 3 |
| PEG-40 stearate | 1 | 1 | 1 | 1 |
| Cetyl Alcohol | 1 | 1 | 1 | 1 |
| White Petrolatum | 0.5 | 0.5 | 0.5 | 0.5 |
| Acetic Acid | 0.1 | 0.1 | 0.1 | 0.1 |
| NaOH | 0.025 | 0.025 | 0.025 | 0.025 |
| EDTA | 0.1 | 0.1 | 0.1 | 0.1 |
| Benzalkonium Chloride | 0.01 | 0.01 | 0.01 | 0.01 |
| Boric Acid | 0.03 | 0.03 | 0.03 | 0.03 |
| NaCl | 0.5 | 0.5 | 0.5 | 0.5 |
| Total | 100 | 100 | 100 | 100 |

TABLE 13

Foam characteristics of the formulations of Table 12.

| | | | | |
|---|---|---|---|---|
| Separation of bulk formula—upon storage at 25° C. for 7 days | ++++ | ++++ | ++++ | ++++ |
| Separation of bulk formula—upon storage at 40° C. for 7 days | ++++ | ++++ | ++++ | ++++ |
| Foam quality after 1 month storage at 5° C. | + | ++ | +++ | ND |
| Foam collapse after storage at 5° C. for 14 days | + | ++ | ++++ | ND |
| Foam collapse after storage at 40° C. for 1 month | ++++ | ++++ | ++++ | ++++ |

As shown in Table 13, foam collapse was accelerated upon storage at 5° C. for 1 month of all the formulations tested. However, increasing the amount of mineral oil from 7% to 9% improved the physical stability of the foam at low temperatures.

Replacements for Cetyl Alcohol

TABLE 14

Formulation #109 with various foaming agents.

| Ingredients | #109 with Cetostearyl alcohol [0.25%-1%] % (w/w) | #109 with Stearyl alcohol [0.25%-1%] % (w/w) | #109 with Stearic acid [0.25%-1%] % (w/w) |
|---|---|---|---|
| Water | [83.7-87.4] | 84.735 | 85.735 |
| Mineral Oil | 7 | 10 | 9 |
| Polysorbate 80 | 3 | 3 | 3 |
| PEG-40 stearate (polyoxyl 40 stearate) | 1 | 1 | 1 |
| Cetyl Alcohol | — | — | — |
| Cetostearyl alcohol | [0.25-1.0] | — | — |
| Stearyl alcohol | — | [0.25-1.0] | — |
| Stearic acid | — | — | [0.25-1.0] |
| White Petrolatum | 0.5 | 0.5 | 0.5 |
| Acetic Acid | 0.1 | 0.1 | 0.1 |
| NaOH | 0.025 | 0.025 | 0.025 |
| EDTA | 0.1 | 0.1 | 0.1 |
| Benzalkonium Chloride | 0.01 | 0.01 | 0.01 |
| Boric Acid | 0.03 | 0.03 | 0.03 |
| NaCl | 0.5 | 0.5 | 0.5 |
| Total | 100 | 100 | 100 |

TABLE 15

Formulations #109 and #109-F used for stability studies

| Ingredients | #109 % (w/w) | #109-F % (w/w) |
|---|---|---|
| Water | 86.385 | 86.285 |
| Mineral Oil | 7 | 7 |
| Polysorbate 80 | 3 | 3 |
| Peg-40 stearate | 1 | 1 |
| Cetyl Alcohol | 1 | 1 |
| White Petrolatum | 0.5 | 0.5 |
| Acetic Acid | 0.1 | 0.1 |
| NaOH | 0.025 | 0.025 |
| EDTA | 0.1 | 0.1 |
| Benzalkonium Chloride | 0.01 | 0.01 |
| Boric Acid | 0.03 | 0.03 |
| NaCl | 0.5 | 0.5 |
| Ciprofloxacin HCl | 0.35 | 0.35 |
| Dexamethasone | — | 0.1 |
| Total | 100 | 100 |

TABLE 16

Stability of Ciprofloxacin in formula #109

| | | | Ciprofloxacin | | Ciprofloxacin Related Substances, % of label claim | | |
|---|---|---|---|---|---|---|---|
| Sample label | Storage conditions | Storage period | % w/w | % of label claim | Ciprofloxacin Ethylenediamine | Ciprofloxacin Formamide | Total |
| #109-C | 25° C. | 6 months | 0.338 | 96.5 | 0.00 | 0.00 | 0.00 |
| #109-C | 40° C. | 6 months | 0.343 | 98.0 | 0.07 | 0.00 | 0.07 |

All formulations showed that cetostearyl alcohol, stearyl alcohol or stearic acid at amounts of 0.5% and 1.0% (w/w of the total weight of the emulsion) can replace cetyl alcohol. The results showed comparable foam quality and foam collapse rate of formulation #109 that has 9% mineral oil.

EXAMPLE 3

Stability of Formulations

Stability of Ciprofloxacin in the Formulations

Stability of ciprofloxacin in formulation #109 (see Table 15 herein above) was evaluated at controlled room temperature and at accelerated aging conditions. The formulation was packed in aluminum canisters, crimped with commercial valves and incubated at 25° C. or 40° C. for different periods of time. Samples from the formulations were taken at zero time (0 months) and after six months of storage and tested by UPLC for the content of ciprofloxacin and its known related/degradation products.

The results presented in Table 16 show that the concentration of Ciprofloxacin did not significantly change upon incubation at 25° C. or 40° C. for up to 6 months. Furthermore, no significant increase was found in the level of substances related to the degradation of Ciprofloxacin. The results thus demonstrate that the formulation developed is chemically stable and displays a potentially long shelf-life. It is well known that storage at 40° C. for 6 months is considered indicative for the stability of a product for not less than 24 months at room temperature.

Stability of Ciprofloxacin and Dexamethasone in the Formulation

Stability of ciprofloxacin and dexamethasone in formulation #109-F (see Table 15 herein above) was evaluated at controlled room temperature and at accelerated aging conditions. The formulation was packed in aluminum canisters, crimped with commercial valves and incubated at 25° C. or 40° C. for different periods of time. Samples from the formulations were taken at zero time (0 months) and at various time points up to three months of storage and tested by UPLC for the content of ciprofloxacin and dexamethasone. The results presented in Table 17 show that the concentration of ciprofloxacin and dexamethasone did not significantly change upon incubation at 25° C. or 40° C. for up to 3 months. The results demonstrate that the formulation #109-F is chemically stable and displays a potentially long shelf-life.

TABLE 17

Stability of Ciprofloxacin and Dexamethasone in formula #109-F

| Formula 109-F | Storage conditions | 0 months | 1.5 months | 3 months |
|---|---|---|---|---|
| Ciprofloxacin | 25° C. | 99.6% | 99.1% | 101.5% |
| [% of label claim] | 40° C. | 99.6% | 98.1% | 95.3% |
| Dexamethasone | 25° C. | 102.3% | 107.2% | 103.1% |
| [% of label claim] | 40° C. | 102.3% | 95.0% | 94.3% |

EXAMPLE 4

Antibiotic Activity of the Formulation

When attempting to validate a method for the microbial enumeration of the formulation according to the US Pharmacopeia, it was found that formulation #109 (see Example 2 herein above) quickly killed all strains of bacteria tested (*Bacillus subtilis* ATCC 6633, *Staphylococcus aureus* ATCC 6538, and *Pseudomonas aeruginosa* ATCC 9027). Various approaches were used including a massive dilution of the formula (at least 800 fold), and a dilution 100 fold of the formulation followed by filtration and rinse of the filter. In all cases the method could not be validated since the recovery of the inoculated bacteria did not meet the Pharmacopeia requirements. Additional tests demonstrated that the antibiotic agent in the formulation was effectively rinsed off the filters, yet due to its high concentration and quick killing action the recovery of bacteria was nil or insufficient. It was therefore concluded that a variety of bacteria could not contaminate the formulation. Quantitative enumeration of fungi such as *Candida albicans* ATCC 10231 and *Aspergillus brasiliensis* ATCC 16404 indicated that formulations (formulation #109 of EXAMPLE 2 herein above) prepared using good manufacturing procedures were found to have less than 1 CFU/gr (i.e. the formulations were not contaminated).

In addition, challenge tests showed that the formulation can prevent contamination that may occur during use or during manufacturing of the product. As shown above, bacterial growth was unfeasible; therefore challenge studies were performed with yeast and molds. The requirements for antimicrobial effectiveness are met if no increase from the initial calculated count for yeast and molds occurs at 7, 14, and 28 days. As shown in Table 18, in the case of formulation #109-C disclosed herein above, not only there was no increase in the initial count, but a drastic 5.0 log reduction for both yeast *Candida albicans* and the mold *Aspergillus brasiliensis* was found after 14 days of storage.

TABLE 18

Antimicrobial effectiveness of formulation #109-C.

| Time point | Candida albicans (ATCC 10231) [CFU/gr] | Aspergillus brasiliensis (ATCC 16404) [CFU/gr] |
|---|---|---|
| After inoculation and before addition of propellant | 500000 | 280000 |
| After addition of propellant | 53000 | 59000 |
| After 7 days | <10 | 50 |
| After 14 days | <10 | <10 |
| After 28 days | <10 | <10 |

The results of Table 16 indicate that if the product is accidentally contaminated during the manufacturing, the preservative and the antibiotic agent present in the formulation will eliminate the microbes introduced and the product will be uncontaminated.

EXAMPLE 5

Clinical Study

A clinical study for assessing the safety, efficacy, and clinical non-inferiority of once a day treatment with a foamable composition designated formula #109-C (that contains only ciprofloxacin as the active ingredient, see Table 19 herein below) in comparison to twice daily application of a commercial ear drop suspension of ciprofloxacin and dexamethasone (Ciprodex® manufactured by Alcon Labs) in the treatment of Acute Diffuse Otitis Externa ("Swimmer's ear") was conducted.

TABLE 19

Ingredients of formulation #109-C.

| Ingredients | #109-C % (w/w) |
|---|---|
| Water | 84.385 |
| Mineral Oil | 9 |
| Polysorbate 80 | 3 |
| Peg-40 stearate | 1 |
| Cetyl Alcohol | 1 |
| White Petrolatum | 0.5 |
| Acetic Acid | 0.1 |
| NaOH | 0.025 |
| EDTA | 0.1 |
| Benzalkonium Chloride | 0.01 |
| Boric Acid | 0.03 |
| NaCl | 0.5 |
| Ciprofloxacin HCl | 0.35 |
| Total | 100 |

The study was open-label, assessor-blinded, randomized, parallel, comparative and multicenter, enrolled 220 subjects aged 6 months and older diagnosed with Otitis Externa of presumed bacterial origin. Inclusion and outcome criteria included the signs and symptoms of the disease: ear edema, ear erythema, ear discharge, and tenderness to movement of the tragus/pinna. The study, complying with GCP guidelines, was performed in 2 hospitals and 8 community clinics in Israel from July to October 2013. The subjects were randomized into one of the two treatment groups: 1) once a day treatment with FoamOtic Cipro, i.e., the otic foam formulation #109-C; or 2) twice a day treatment with commercial ear drops Ciprodex® manufactured by Alcon Labs. From the 220 patients enrolled, 199 subjects were found eligible to be included in the "Per Protocol" analysis set that consisted of 97 subjects that were treated with the otic foam treatment and 102 subjects that were treated with ear drops.

Both treatments continued for 7 days. Microbial cultures were taken from the subjects at baseline visit (considered day 1), at a visit during treatment, and post-treatment at the test-of-cure visit (Visit 3, days 8-11). Upon completion of the treatment, the signs and symptoms of the infection were assessed and compared to baseline. Subjects were considered "Cured" if the physician considered that no additional antibiotic treatment was needed at the test of cure visit (Visit 3) while subjects were considered treatment "Failure" if an additional antibiotic treatment was needed. In order to measure the time to end of pain subjects were requested to fill twice daily a pain dairy according to a visual analogue scale (VAS) being zero (0) no pain and 10 the highest conceivable pain. Data from young children was collected using a "Faces Pain Scale" with scores of 0, 2, 4, 6, 8, or 10, being '0'='no pain' and '10'='very much pain'. Time to end of pain was defined as the time lapsed from the first dose taken to the first instance in which the pain score reported is zero (0) being zero (0) all the subsequent pain scores reported.

The results in Table 20 show that the cure rates of FoamOtic applied once daily and Ciprodex® applied twice daily were similar. The percentage of cured subjects was 94.85% in the foam treated group (92 out of 97 subjects) and 96.08% in the Ciprodex® group (98 out of 102). The failure rates were 5.15% and 3.92% for the foam treated and Ciprodex® treated group, respectively. The differences found were not statistically significant (p-value of Fisher exact test 0.7429).

TABLE 20

Clinical results (per protocol analysis).

| Treatment arm | Cure rate (subjects that did not require additional antibiotic therapy) | Failure rate (subjects that required additional antibiotic therapy) |
|---|---|---|
| FoamOtic | 94.85% (92/97) | 5.15% (5/97) |
| Ciprodex ® | 96.08% (98/102) | 3.92% (4/102) |

The results therefore indicate that once-daily treatment with the otic foam (Formulation #109-C) which contains ciprofloxacin as the sole active ingredient was as efficient as twice daily application of commercial ear drops which contain two active ingredients: ciprofloxacin and dexamethasone. It is to be emphasized that the concentration of ciprofloxacin in the foam formulation and in the ear drops was identical.

In addition, there were no differences in the levels of cure rates observed for FoamOtic and Ciprodex® in children and adults. In children (subjects aged 6 months to 18 years old) the cure rate achieved in the foam-treated group was 96.30% while the cure rate in the Ciprodex®-treated group was 95.74%. Similarly, in adults, the cure rate achieved by the Foam was 93.02% and in the Ciprodex® group was 96.36% (see Table 21). The differences found were not statistically significant (p-value of Fisher exact test 1.000 and 0.6512 for children and adults, respectively).

TABLE 21

Cure rates achieved in children and adults treated with FoamOtic or Ciprodex ®

| Age group | Treatment arm | Cure rate (subjects that did not require additional antibiotic therapy) | Failure rate (subjects that required additional antimicrobial therapy) |
|---|---|---|---|
| Children | FoamOtic | 96.30% (52/54) | 3.70% (2/54) |
| | Ciprodex ® | 95.74% (45/47) | 4.26% (2/47) |
| Adult | FoamOtic | 93.02% (40/43) | 6.98% (3/43) |
| | Ciprodex ® | 96.36% (53/55) | 3.64% (2/55) |

Time to end-of-pain: Kaplan-Meier survival curves based on the censored data of the pain dairies showed that the time to end of pain was similar between the two treatment groups (p value of log-rank test=0.8163, FIG. 1) The median time to end of pain was 3.97 days in the FoamOtic group and 4.58 days in the Ciprodex treated group (Table 22 below). Comparable results were obtained when looking at the 75 and 25 percentile. Therefore, FoamOtic containing only ciprofloxacin and applied once daily stopped the pain in a similar way as ear drops applied twice daily that contain a steroid (dexamethasone) in addition to ciprofloxacin.

TABLE 22

Estimated time to end of pain in the groups of subjects treated with FoamOtic or Ciprodex ®

| | Time to end of pain (days since treatment start) | |
|---|---|---|
| Quartile estimates | FoamOtic (n = 97) | Ciprodex ® (n = 102) |
| 75 | 6.49 | 6.48 |
| 50 | 3.97 | 4.58 |
| 25 | 2.63 | 2.85 |

Thus, the present results demonstrate the clinical efficacy of the otic foam compared to commercial ear drops. The results show that when administered once daily in the form of otic foam, a lower dose of ciprofloxacin in the absence of an anti-inflammatory steroid provides the same relief as the combination of ciprofloxacin and dexamethasone in the form of ear drops applied twice daily.

These results clearly indicate that the otic foam of the present invention presents an advantage over commercially ear drops by achieving the desired therapeutic effect in treating acute otitis externa with approximately half of the amount of the antibiotic agent and without the need of the steroid present in the Ciprodex® pharmaceutical composition applied twice daily.

It will be appreciated by persons skilled in the art that the present invention is not limited by what has been particularly shown and described herein above. Rather the scope of the invention is defined by the claims that follow.

The invention claimed is:
1. A foamable otic pharmaceutical composition comprising:
  (a) an oil-in-water emulsion comprising:
    (i) an antibiotic agent in an amount effective for antibacterial action;
    (ii) an analgesic or anesthetic agent;
    (iii) water in an amount of at least 75% (w/w) of the total weight of the emulsion;
    (iv) mineral oil in an amount of no more than 15% (w/w) of the total weight of the emulsion;

(v) a synthetic surfactant pharmaceutically acceptable for otic use;
(vi) a foaming agent selected from a fatty alcohol and a fatty acid;
(vii) white petrolatum in an amount that does not exceed 3% (w/w) of the total weight of the emulsion; and
(b) a compressed propellant gas;
wherein the oil-in-water emulsion is devoid of organic polar co-solvents, the organic polar co-solvents being polyols,
wherein the oil-in-water emulsion has an osmolarity of about 280 mOsm/L to about 320 mOsm/L, and
wherein the composition, packaged in a container, is adapted to form a foam after dispensing from the container.

2. The foamable otic pharmaceutical composition according to claim 1, wherein the antibiotic agent is a quinolone antibiotic agent.

3. The foamable otic pharmaceutical composition according to claim 2, wherein the quinolone antibiotic agent is selected from the group consisting ciprofloxacin, ofloxacin, moxifloxacin, levofloxacin, marbofloxacin, enrofloxacin, finafloxacin, besifloxacin, 7-[(3E)-3-(2-Amino-1-fluoroethylidene)-1-piperidinyl]-1-cyclopropyl-6-fluoro -1,4-dihydro-8-methoxy-4-oxo-3-quinolinecarboxylic acid (JNJ-Q2), orbifloxacin, delafloxacin, pradofloxacin, and salts thereof.

4. The foamable composition according to claim 3, wherein ciprofloxacin is ciprofloxacin HCl.

5. The foamable composition according to claim 1, wherein the analgesic or anesthetic agent is selected from the group consisting of benzocaine, tetracaine, procaine, and antipyrine.

6. The foamable otic pharmaceutical composition according to claim 1, wherein the synthetic surfactant is selected from the group consisting of polysorbates, tylaxopol, glyceryl stearate, PEG stearate, polyoxyethylene fatty acid esters, polyoxyethylene alkyl ethers, and combinations thereof.

7. The foamable otic pharmaceutical composition according to claim 1, wherein the fatty alcohol is selected from the group consisting of cetyl alcohol, stearyl alcohol, and cytostearyl alcohol.

8. The foamable otic pharmaceutical composition according to claim 1, wherein the polyol is selected from the group consisting of glycerol, propylene glycol, hexylene glycol, diethylene glycol, and propylene glycol n-alkanol.

9. The foamable otic pharmaceutical composition according to claim 1, further comprising at least one excipient selected from the group consisting of a tonicity agent, a pH modifying agent, disodium edetate, an antibacterial agent, an anti-oxidant, a preservative, and a gelling agent.

10. The foamable otic pharmaceutical composition according to claim 1, wherein the compressed propellant gas is a mixture of hydrocarbons present in an amount ranging from about 1% to about 8% by weight of the composition.

11. The foamable otic pharmaceutical composition according to claim 1, wherein the oil-in-water emulsion comprises:
Ciprofloxacin hydrochloride;
(ii) an analgesic or anesthetic agent;
(ii) water in an amount ranging from 75% to 88% (w/w);
(iii) mineral oil in an amount of 7% to 10% (w/w);
(iv) PEG-40 stearate and glyceryl stearate;
(v) cetyl alcohol in an amount of about 0.25% to about 2% (w/w); and
(vi) white petrolatum in an amount of about 0.1% to about 1% (w/w).

12. The foamable otic pharmaceutical composition according to claim 11, further comprising a tonicity agent, a pH modifying agent, disodium edetate, and a gelling agent.

13. The foamable otic pharmaceutical composition according to claim 11, further comprising dextrose as a tonicity agent, acetic acid and sodium acetate as pH modifying agents, disodium edetate, and hydroxyethylcellulose and polyvinylpyrollidone as gelling agents.

14. The foamable otic pharmaceutical composition according to claim 13 comprising ciprofloxacin HCl and an analgesic or anesthetic agent as active agents, and further comprising the following excipients:

| Excipients | % (w/w) |
| --- | --- |
| Water | To complete to 100 |
| Mineral oil | 7 |
| PEG-40 stearate and glyceyl stearate | 6 |
| Cetyl alcohol | 1.5 |
| White petrolatum | 1 |
| Dextrose | 0.5 |
| Acetic acid | 0.1 |
| Sodium acetate | 0.1 |
| EDTA (disodium edetate) | 0.1 |
| Hydroxyethyl cellulose | 0.3 |
| polyvinylpyrrolidone | 1.2. |

15. A method for treating an ear disorder comprising administering to the ear of a subject in need of such treatment a therapeutically effective amount of a foamable otic pharmaceutical composition according to claim 1.

16. The method according to claim 15, wherein the ear disorder is selected from the group consisting of external ear disorders, middle ear disorders, and inner ear disorders.

17. The method according to claim 16, wherein the external ear disorder is otitis externa.

* * * * *